(12) United States Patent
Naranjo-Tackman et al.

(10) Patent No.: US 9,655,781 B2
(45) Date of Patent: *May 23, 2017

(54) LASER SYSTEM AND METHOD FOR CORRECTION OF INDUCED ASTIGMATISM

(71) Applicant: LensAR, Inc., Orlando, FL (US)

(72) Inventors: Ramón Naranjo-Tackman, Mexico City (MX); Jorge Octavio Villar Kuri, Col. San Lucas Coyoacán (MX); Rudolph W. Frey, Winter Park, FL (US)

(73) Assignee: Lensar, Inc., Orlando, FL (US)

( * ) Notice: Subject to any disclaimer, the term of this patent is extended or adjusted under 35 U.S.C. 154(b) by 518 days.

This patent is subject to a terminal disclaimer.

(21) Appl. No.: 14/142,255

(22) Filed: Dec. 27, 2013

(65) Prior Publication Data

US 2014/0155874 A1   Jun. 5, 2014

Related U.S. Application Data

(63) Continuation of application No. 12/831,859, filed on Jul. 7, 2010, now Pat. No. 8,617,146.

(60) Provisional application No. 61/228,533, filed on Jul. 24, 2009.

(51) Int. Cl.
*A61F 9/008* (2006.01)

(52) U.S. Cl.
CPC ...... *A61F 9/00825* (2013.01); *A61F 9/00829* (2013.01); *A61F 2009/0087* (2013.01); *A61F 2009/00872* (2013.01); *A61F 2009/00889* (2013.01)

(58) Field of Classification Search
CPC .... A61F 2009/0087; A61F 2009/00872; A61F 2009/00889; A61F 9/00825; A61F 9/00829
USPC .............................................. 606/4–6, 10–12
See application file for complete search history.

(56) References Cited

U.S. PATENT DOCUMENTS

| | | | |
|---|---|---|---|
| 5,984,916 A * | 11/1999 | Lai | B23K 26/0624 606/10 |
| 8,382,745 B2 * | 2/2013 | Naranjo-Tackman | A61F 9/008 606/10 |
| 8,617,146 B2 * | 12/2013 | Naranjo-Tackman | A61F 9/00825 606/10 |
| 2010/0324543 A1 * | 12/2010 | Kurtz | A61F 9/008 606/6 |

* cited by examiner

*Primary Examiner* — Christopher A Flory
*Assistant Examiner* — Jonathan Kuo
(74) *Attorney, Agent, or Firm* — Glen P. Belvis; Steptoe & Johnson, LLP.

(57) ABSTRACT

There is provided a system, apparatus and methods for developing laser systems that can create precise predetermined clear corneal incisions that are capable of reducing induced astigmatism. The systems, apparatus and methods further provide laser systems that can provide these incisions at or below Bowman's membrane.

10 Claims, 2 Drawing Sheets

LASER SYSTEM AND METHOD FOR CORRECTION OF INDUCED ASTIGMATISM

This application is a continuation of U.S. patent application Ser. No. 12/831,859, filed on Jul. 7, 2010 (pending), which claims the benefit of priority of provisional application Ser. No. 61/228,533 filed Jul. 24, 2009, the disclosures of each of which are incorporated herein by reference.

BACKGROUND OF THE INVENTION

The present invention relates to methods and systems for improving procedures that address cataracts, opacifications in the lens, clear lens extraction, removal of natural lens material, use of lens replacement materials and combinations thereof. Specifically, the present invention relates to systems and methods that provide predetermined, precise and reproducible laser shot patterns for creating cuts in the cornea of the eye in predetermined and precise shapes that are reproducible from patient to patient and surgeon to surgeon and which address aberrations in the eye.

The established treatment for cataracts is the removal of the opacified human crystalline lens and its replacement with an IOL. In general, IOLs consist of a small plastic lens with plastic side struts, called haptics, to hold the lens in place within the capsular bag inside the eye. Exemplary types of IOLs include monofocal lenses, multifocal IOLs which provide the patient with multiple-focused vision at far and reading distance, and accommodative IOLs which provide the patient with visual accommodation. The flexible nature of many IOLs enables them to be rolled and/or folded up for insertion into the capsule. Examples of IOLs are found in U.S. Pat. Nos. 7,188,949, 6,849,091, 5,699,142 and 5,607,472, the disclosures of which are incorporated herein by reference. Commercially available IOLs that, by way of example, may benefit from the present invention are CRYSTALENS and ACRYSOF RESTOR.

The CRYSTALENS IOL was developed by Eyeonics and is presently provided by Bausch & Lomb. It is at least in part believed to be disclosed in U.S. Pat. No. 6,849,091. Further information regarding its structure and efficacy is provided by Food and Drug Administration (FDA) PMA P030002 and related documents to that PMA file. The FDA approved indicated use for CRYSTALENS was in part: "The Crystalens™ Model AT-45 Accommodating IOL is intended for primary implantation in the capsular bar of the eye for visual correction of apkakia in adult patients in whom a cataractous lens has been removed and is intended to provide near, intermediate, and distance vision without spectacles. The Crystalens™ IOL provides approximately one diopter of monocular accommodation." (Nov. 14, 2003 PMA P030002 at Part 2, Summary of Safety and Effectiveness Data, ¶ INDICATIONS FOR USE).

Thus, the CRYSTALENS is an example of an FDA approved accommodating IOL. The term "FDA approved accommodating IOL" refers to any IOL that has obtained FDA approval having an indicated use that provides for accommodation, regardless of whether the IOL is actually being employed for such an approved use.

The ACRYSOF RESTOR IOL is provided by Alcon, it is at least in part believed to be disclosed in U.S. Pat. No. 5,669,142. Further information regarding its structure and efficacy is provided by FDA PMA P040020 and related documents to that PMA file. The FDA approved use for RESTOR was in part: "AcrySOF® ReSTOR® IOLs are indicated for the visual correction of aphakia secondary to removal of a cataractous lens in adult patients with and without presbyopia, who desire near, intermediate and distance vision with increased spectacle independence. The lens is intended to be placed in the capsular bag." (Apr. 24, 2004, PMA P040020, at Part 2, Summary of Safety and Effectiveness Data, ¶INDICATIONS).

Thus, the RESTOR is an example of an FDA approved IOL for near, intermediate and distance vision. The term "FDA approved IOL for near, intermediate and distance vision" refers to any IOL that has obtained FDA approval having an indicated use that provides for near, intermediate and distance vision, regardless of whether the IOL is actually being employed for such an approved use. The CRYSTALENS would also be an example of an FDA approved IOL for near, intermediate and distance vision. Moreover, the RESTOR and CRYSTALENS are examples of an FDA approved IOLs that reduce and/or eliminate the need for spectacles.

The removal of the natural crystalline lens and replacement with a lens replacement material employ the use of a small initial incision or incisions in the limbal area of the eye, which is the transition area between the cornea and sclera. This initial incision is typically made with a small triangular blade that is pushed into the limbal area of the eye. It is through this initial incision that other instruments for use in the removal and replacement of natural lens material are inserted, and also it is through this incision that the natural lens material is removed from the eye and replacement lens material inserted into the eye.

Once the initial incision has been made, the removal of the opacified natural crystalline lens and replacement with a lens replacement material, such as an FDA approved IOL, presently employ a capsulorhexis and/or a capsulotomy. A capsulorhexis generally consists of the removal of a part of the anterior lens capsule and the creation of a hole or opening in the lens capsule that results from at least in part a tearing action. A capsulotomy generally consists of a cutting of the lens capsule, without or with minimum tearing of the capsule. Thus, to remove the opacified natural lens material, the lens capsule is opened. There are several known techniques for performing a capsulorhexis and a capsulotomy. These would include the technique known as a can opener approach, a Continuous Curvilinear Capsulorhexis (CCC) and the use of a Fugo plasma blade.

SUMMARY

It is desirable to develop systems that would provide greater control in the creation of the incisions and make these improvements patient and surgeon independent, or at least, reduce the variability from patient-to-patient and surgeon-to-surgeon.

The novel and improved methods and systems for the performance of incisions in the cornea in the area of Bowman's membrane, which comprise aspects of the present inventions and which are set forth in detail in the present patent specification, may provide for better implementation of other methods and systems for delivering laser beams to the lens of the eye, such as those disclosed in published applications US 2007/173794A1, US 2007/173795A1, US 2007/185475A1, WO 2007/084694 A2, and WO 2007/084627A2, the disclosures of which are incorporated herein by reference.

The present invention, among other things, solves this need by providing greater control in the creation of a precise and predetermined incision to the cornea in the area of Bowman's membrane to correct for astigmatism that may be present after replacement of the natural lens of the eye with artificial lens material. Thus, there is provided herein a system and method to perform.

Provided herein are embodiments of the present invention. Thus, there is provided herein a a system for providing laser shot patterns to an eye, the system comprising a therapeutic laser that produces a laser beam, a laser shot pattern for performing a capsulotomy, a laser shot pattern for sectioning a lens of an eye and, a laser shot pattern for proving a sub-Bowman's membrane arcuate cut in the cornea. Thus, the laser system is capable of providing the arcuate cut in a manner that does not disrupt Bowman's membrane and reduces induced astigmatism. These arcuate patterns may be oriented along the steep axis, have about a 3 mm radius, have an arc of about 60°, of about 90° and from about 60° to about 90°. Further the system may have an arcuate pattern that has an arc of about less than 90° and about greater than or equal to 60°, an arcuate pattern has about a 3 mm radius and an arc of about 90° to about 60°.

There is also provided a system for reducing induced astigmatism associated with replacement of a natural human lens with a lens replacement material, the system comprising: a laser for providing a laser beam; a controller having associated with it a shot pattern; the shot pattern comprising two arcuate patterns oriented on the eye along the steep axis; and, the system capable of delivering the laser beam in the shot pattern below Bowman's membrane to treat astigmatism.

There is further provided a system having a therapeutic laser for producing a laser beam, a laser shot pattern for proving a pair of arcuate cuts in the cornea, the shot pattern having a depth of about less than or equal to the thickness of the cornea. The system is thus capable of providing the arcuate cuts in a manner that does not disrupt the epithelium of the eye and reduces induced astigmatism.

There is yet further provided arcuate patterns of these systems wherein the arcuate pattern is oriented along the steep axis, the arcuate pattern has about a 3 mm radius, the arcuate pattern has an arc of about 60°, the arcuate pattern has an arc of about 90°, and the arcuate pattern has an arc of about less than 90° and about greater than or equal to 60°.

There is additionally provided a method for performing cataract surgery and reducing induced astigmatism by using a laser system comprising: first, positioning an eye of a patient with respect to the laser system; second, directing the laser system to perform a capsulotomy on the eye; and, third, directing the laser system to deliver a pair of arcuate laser shot patterns to the cornea of the eye, thereby reducing astigmatism while not disrupting the epithelium.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE DRAWINGS AND THE PREFERRED EMBODIMENTS

In general, the present inventions relate to methods and systems for providing a laser to the cornea of the eye to address, improve and correct aberrations of the eye. In particular, the present inventions relate to methods and systems for addressing aberrations of the eye that are present prior to and after the natural human crystalline lens has been removed and replaced with a lens replacement material and in particular to address astigmatism.

The present methods and systems can be used with the novel and innovative laser system techniques that are the subject of the co-pending patent applications that are cited herein and which have been incorporated herein by reference, and the present methods and systems may possibly be used with other laser delivery systems for the removal of lens material to the extent such systems may be developed in the future. Preferably, the present methods and systems can be incorporated into and used in conjunction with the systems of the co-pending applications that have been incorporated herein by reference. In this way a single system, with a single therapeutic laser, can perform the cuts necessary to remove and replace the natural lens and correct any remaining aberrations.

Novel and pioneering laser systems and methods for the removal and replace of lens material are disclosed in regular and provisional U.S. patent application Ser. No. 61/228,506, Ser. No. 61/228,529, Ser. No. 61/228,484, Ser. No. 12/509,412, and Ser. No. 12/509,211, which applications were filed on the same day as the present application, and the disclosures of which are incorporated herein by reference.

Thus, in general, the present invention provides for a laser system, i.e., a laser device for delivering a laser to the cornea of the eye. In general the laser system has a treatment or therapeutic laser, optics for delivering the laser beam from the treatment laser to the eye, and a particular pattern which provides for the placement of treatment laser shots in the cornea to create arcuate area of tissue removal, i.e., cuts, below the surface of the cornea and in the general area of Bowman's membrane.

Figure 1:
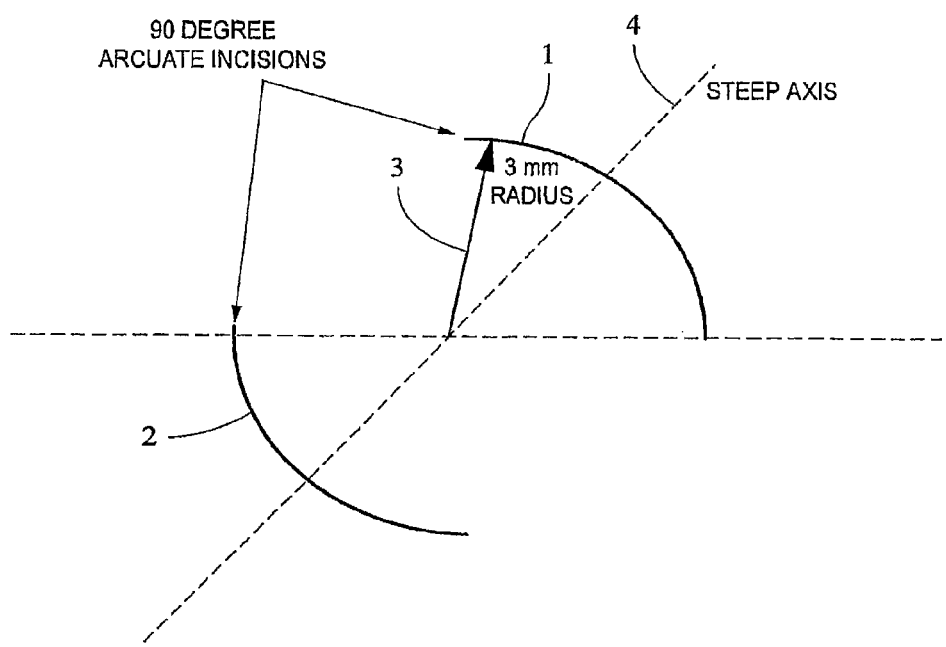
FIG. 1 is a schematic diagram of arcuate patterns of the present invention.

Referring now to FIG. 1 there is provided an example of a clear corneal incision (CCI) in an arcuate pattern and resultant arcuate cuts of the present invention. Thus, there is provided a first arcuate cut pattern 1 and a second arcuate cut pattern 2. These arcuate cut patterns have a 3 mm radius, shown by arrow 3, and have an arc of 90°. The cut patterns 1 and 2 are oriented along the steep axis 4. Note that one of ordinary skill in the art of correction of astigmatism would readily understand that the steep axis 4 regards an axis of curvature of the cornea that is steeper in curvature than another axis of curvature of the cornea. In this example the patterns and resultant cuts are entirely below Bowman's membrane and in this manner they are made without cutting through or disrupting the epithelium and without cutting through or disrupting Bowman's membrane. The pattern and resultant cut have a depth or thickness that is approximately 90% of the remaining thickness of the cornea.

Further embodiments and variations of this example would include patterns less than 90° and greater than and including 60° degrees. It is presently believed that the 90° arc pattern is an appropriate treatment of −4 to −6 cylinder diopters of astigmatism and the 60° arc pattern is an appropriate treatment for −2 to −3.5 cylinder diopters. The depth of the cuts can be from about 90% of the thickness of the cornea to about 60% of the cornea, and from about 518 µm to about 400 µm. Although it is preferred that the cuts be below Bowman's membrane, and thus not disturb that membrane and the structures anterior to it, it is contemplated that the cuts may be made slightly above, at or starting on, or slightly below that membrane. The radius of the CCI can range, from about 2.6 to 3.2 mm and preferably are about 3 mm. The amount of astigmatic correction is dependant upon the radius of the CCI Employment of the CCIs of the present invention can be to correct astigmatism that is present prior to any cataract treatment, that is caused in whole or in part by a cataract treatment, and that is residual after a cataract treatment, whether caused by the treatment or not. Thus, as used herein, astigmatic aberrations that are brought about by, or develop as a result of treatments to the eye, such as replacement of the natural crystalline lens with a lens replacement material are referred to herein as induced astigmatism or induced astigmatic aberrations.

Figure 2:
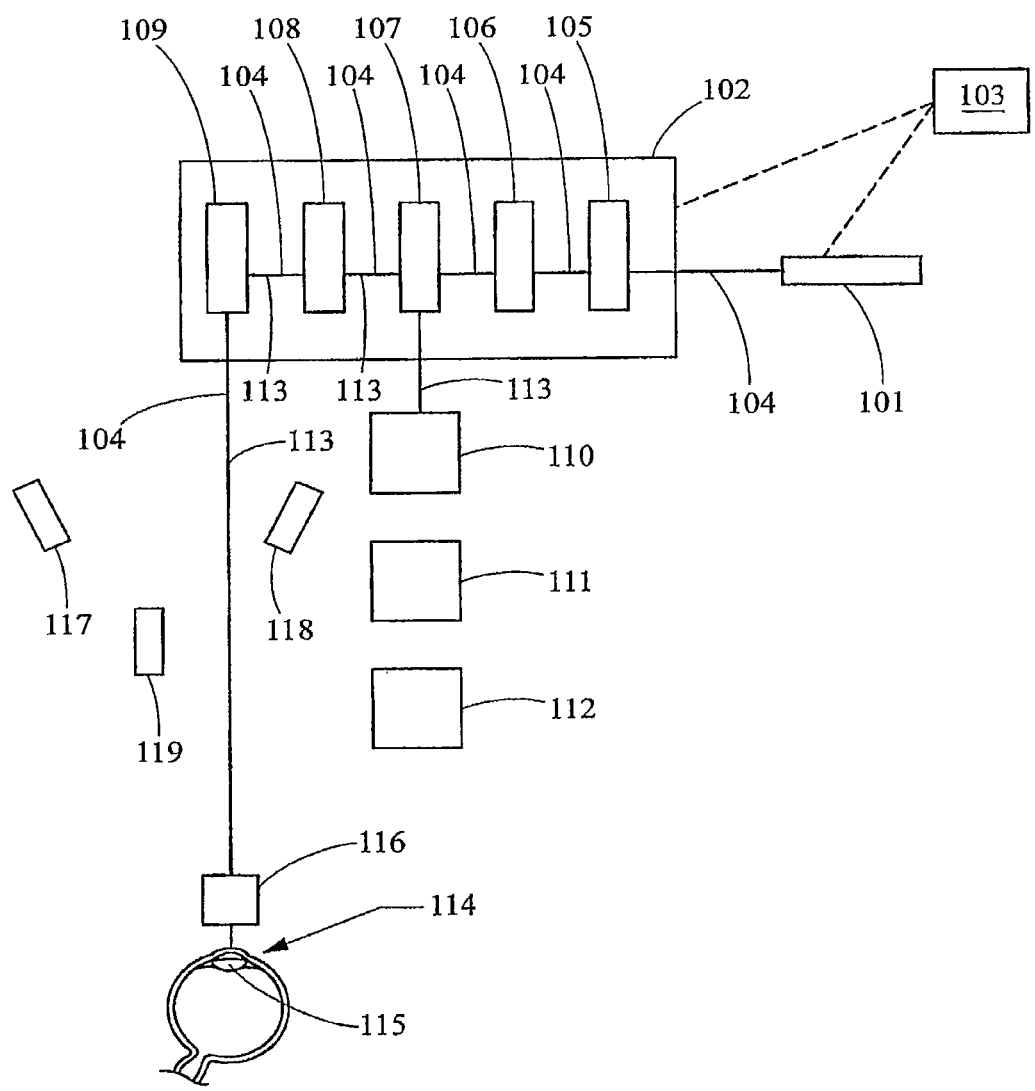
FIG. 2 is a schematic diagram of system for delivering the arcuate patterns of the present invention.

Thus, in general a preferred laser system, i.e., a laser device, for treating patients is provided as shown by way of example in FIG. 2. In this system there is provided a treatment laser 101; optics for delivering the laser beam 102; a control system for delivering the laser beam to the lens in a particular pattern 103, which control system 103 is associated with and/or interfaces with the other components of the system, as shown for example by dashed lines in FIG. 2, and/or other control systems not shown in FIG. 2.

In general, a laser system for providing the arcuate pattern and creating the resultant arcuate cuts in the cornea has by way of example and referring to FIG. 2, a treatment laser 101 which should provide a beam 104. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the conversion of matter to a gas by the laser. The term photodisruption has also been generally referred to as Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in 2007/084694 A2 and WO 2007/084627A2, which are incorporated herein by reference. These and other similar lasers may be used as therapeutic lasers. For procedures on the cornea the same type of therapeutic laser as described herein may be used, with the energy and focal point being selected to perform the desired procedure.

In general, the optics for delivering 102 the laser beam 104 to the structures of the eye should be capable of providing a series of shots to the natural lens in a precise and predetermined pattern in the x, y and z dimension. The z dimension as used herein refers to that dimension which has an axis that corresponds to, or is essentially parallel with the A-P axis of the eye. The optics should also provide a predetermined beam spot size to cause photodisruption with the laser energy reaching the structure of the eye intended to be cut.

In general, the control system 103 for delivering the laser beam 104 may be any computer, controller, and/or software hardware combination that is capable of selecting and controlling x y z scanning parameters and laser firing. These components may typically be associated at least in part with circuit boards that interface to the x y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the slit scanned laser and/or from a separate controller for the slit scanned laser system.

The laser optics for delivering 102 the laser beam 104 comprise a beam expander telescope 105, a z focus mechanism 106, a beam combiner 107, an x y scanner 108, and focusing optics 109. There is further provided relay optics 110, camera optics 111, which include a zoom, and a first ccd camera 112.

Optical images of the eye 114 and in particular optical images of the natural lens 115 of the eye 114 are conveyed along a path 113. This path 113 follows the same path as the laser beam 104 from the natural lens 115 through the laser patient interface 116, the focusing optics 109, the x y scanner 108 and the beam combiner 107. There is further provided a laser patient interface 116, a structured light source 117 and a structured light camera 118, including a lens. Examples of patient interface and related apparatus that are useful with the present system are provided in regular and provisional U.S. patent application Ser. No. 12/509,021 and Ser. No. 61/228,457, wherein each was filed on the same day as the present application. The disclosures of which are incorporated herein by reference.

A structured light source 117 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 119.

When using a scanned slit illumination the operation includes positioning the slit on one side of the lens, taking an image then moving the slit approximately one slit width, then taking another image, and then repeating this sequence until the entire lens is observed. For example, a 100 µm slit width can scan a nominal 9 mm dilated pupil diameter in 90 images, which takes approximately 3 seconds using a 30 Hz frame rate camera. To obtain images of the anterior surface in a single image without overlap, the slit should be at an angle to the AP axis, i.e., it should not be parallel to that axis. The nominal slit angle can be approximately 15 to 30 degrees from the AP axis. Any visible or near IR wavelength source within the sensitivity of the camera may be used. Low coherence length sources are preferable to reduce speckle noise.

The structured light illumination source 117 and the structured light camera 118 are arranged in an angled relationship. The angled relationship may be but is not required to be in the so-called Scheimpflug configuration, which is well-known. The structured light source 117, in conjunction with the slit scanning means 119, projects a line and or a plurality of lines onto the eye lens 115 at an angle or plurality of angles. The light scattered at the eye lens 115 forms the object to be imaged by the lens 247 and focused onto the camera system 118. Since the slit illuminated image in the eye lens 115 may be at a large angle with respect to the camera 118, this presents a large depth of field to the camera and the entire slit image may not be in sharp focus at the camera. By tilting the camera at an angle or plurality of angles the image along the illuminated plane can be in sharper focus. To the extent that a shaper focus is not obtained, arithmetic data evaluation means are further provided herein to determine a more precise location of the illuminated structures with respect to the laser device.

The images from the camera 118 may be conveyed to the controller 103 for processing and further use in the operation of the system. They may also be sent to a separate processor and/or controller, which in turn communicates with the controller 103. The structured light source 117, the camera 118 and the slit scanning means 119 comprise a means for determining the position and apex of the lens in relation to the laser system.

The delivery of laser shot patterns for the removal of lens material is provided. Thus, there are provided methods and systems for producing cuts, i.e., incisions in the anterior lens capsule. These cuts are created by the therapeutic laser beam 104 being delivered to the anterior lens capsule in precise, predetermined and highly reproducible patterns, which delivery results in precise, predetermined and highly reproducible shaped cuts in patterns as described and taught herein, or as may be called for by the use of a particular IOL or other device or material to be inserted within the lens capsule. As used herein geometric shaped patterns or cuts referrer to circular and elliptical shaped patterns or cuts. As used herein, non-geometric shaped patterns or cuts refers to all other shapes that are not circular or elliptical.

The methods and systems to create these cuts in the anterior capsule provide superior results to the handheld methods and apparatus previously known for performing capsulorhexis and capsulotomy, and thus, the methods and systems disclosed herein are considered to be a substantial advancement in these techniques. In addition the delivery of the laser beam shots in a manner that greatly reduces the risk of a missed cut, which depending upon the particular application may be very significant is provided. Moreover, as provided in the following examples, anterior capsule cuts are envisioned and provided that may be a continuous cuts, cuts and lands (uncut capsule portions between cuts) and perforations. Thus, as used herein the terms "missed cut" or "missed cuts" refer to a cut that was intended to be carried out by the delivery of a particular laser shot pattern, but which did not occur because the laser beam missed the lens capsule or targeted lens material. Thus, in a cut and land pattern the lands would not be considered missed cuts, if they were intended to be left uncut by the laser pattern.

The cuts in the lens anterior surface are for the purpose of creating an opening in the lens capsule for the remove of the interior structures of the lens. To facilitate this removal there are provided various laser shot patterns that cut the interior structure of the lens into small volumes, which volumes can then be removed from the lens capsule. These small volumes can range from about 1 mm$^2$ to about 16 mm$^2$ and more preferably from about 2.5 mm$^2$ to about 4 mm$^2$. Thus a grid laser shot pattern within the interior structures of the lens, which creates cube shaped volumes of interior lens material, can be employed. These cubes can range in size from a side having a length of about 100 μm to about 4 mm, with about 500 μm to 2 mm being a preferred size. Additionally, this invention is not limited to the formation of cubes and other volumetric shapes of similar general size may be employed. For example arrangement of other shapes such as triangles and pie sliced volumes may be employed.

The laser cut in the anterior capsule is used to create a small opening in the lens anterior surface of the lens capsule for removal of the sectioned volumes of interior material. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens material the lens capsule would subsequently house a suitable replacement, such as an IOL, accommodative IOL, or synthetic lens refilling materials. Moreover, the size and the shape of the opening is variable and precisely controlled and preferably for presently known lens refilling materials and IOLs is 2 mm or less diameter for lens refilling applications and about 5 mm for IOLs.

The order in which these activities are performed may depend upon the particular characteristics of the internal lens structure, the density of the cataract, the position of the cataract, the type of device used to remove the internal lens material once it has been sectioned into small volumes, the type and power of the laser used, the amount and size of gas bubbles that are produced by the laser, and other factors, Thus, although the examples herein provide for an order of performing the activity of cutting the anterior surface of the lens and sectioning the interior structures of the lens, it should be recognized that this order can be changed, as well as, performed essentially simultaneously or simultaneously.

The preferred laser system for treating patients is capable of making precise and predetermined cuts in the capsule of the lens thus giving rise to capsulotomies that are of precise and predetermined shapes. Thus, there is provided the method of obtaining and analyzing the shape and structure of an IOL, and in particular obtaining and analyzing the shape and structure of an accommodating IOL, an IOL that reduces and/or eliminates the need for spectacles, and/or an IOL for near, intermediate and distance vision, including but limited to FDA approved versions of said IOLs. Based upon this analysis an optimized shape and position for the capsulotomy for use with a particular IOL, or grouping of similarly shaped IOLs, is determined. A predetermined shot pattern for making this optimized shaped capsulotomy is then provided to the laser system, preferably by providing the shot pattern to the control system 103. The laser system can then be used for any one or all of the following procedures, determining the shape and position of the anterior surface of the lens, and in particular the anterior surface of the lens capsule, determining the apex of the lens capsule in relation to the laser system, performing a laser capsulotomy having the precise and predetermined shape selected for a particular type of IOL, and removal of the natural lens material.

Thus, there is provided techniques, systems and apparatus to deliver laser beam in a shot pattern to the lens of the eye and in particular to the capsule of the lens of the eye in a precise and predetermined manner to provided for a precise predetermined capsulotomy. The shape of these patterns may be delivered using either the jigsaw or ring delivery sequences.

There is further provided herein the use of laser shot patterns having a large range of Z swept at a high rate of speed, while the XY position is moved in a circular, or elliptical or other pattern or desired shape, more slowly so that the laser cutting action occurs multiple times over essentially the same XY position. Thus, it could be envisioned that the laser beam is operating like the tip of a jigsaw blade moving up and down rapidly compared to the XY positioning to create the cut shape. In this way, if the anterior capsule shifts during the cut, due to gas bubble propagation or any other reason, the cut will still be made to the capsule, albeit perhaps outside the center region of the z direction up-down distribution of shots, and more to the anterior or posterior ends of that distribution. For laser cutting of the nucleus where a great deal of bubble buildup is created, a Z range, or up-down range of the cut should be approximately 1 mm in extent, nominally centered on the anterior capsule which would allow approximately +/−475 μm of capsule movement and still provide cutting of a 25 μm thick capsule.

In addition to enabling cutting of a capsule that moves move during the procedure, this procedure can be used to compensate for static errors in capsule position due to for example measurement errors. In this way the extent of the Z range may be increased by the known error of the system.

In addition to the large Z range sweeps disclosed herein, there is also contemplated the use of a smaller Z range of cut motion for the case where the uncertainty in capsule position from both static measurement error and anticipated change in position might be smaller, perhaps in the range of hundreds of μm or in the case of highly precise measurement data and near zero movement of the capsule during surgery. In such a case the Z range could be tens of μm—enough range to cut through the capsule thickness.

Further methods and systems to define a high accuracy position measurement of structures of the eye and in particular the anterior capsule, so as to provide in general greater accuracy, precisions and reproducibility from patient to patient for procedures on the eye and in particular capsulotomies, is provided in regular U.S. patent application Ser. No. 12/509,412, the entire disclosure of which is incorporated herein by reference.

In the laser shot patterns provided herein it is preferred that the placement of individual shots with respect to adjacent shots in the pattern are sufficiently close enough to each other, such that when the pattern is complete a sufficiently continuous layer and/or line and/or volume of material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock wave propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz, which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption. The terms first, second, third, etc. as used herein are relative terms and must be viewed in the context in which they are used. They do not relate to timing, unless specifically referred to as such.

From the foregoing description, one skilled in the art can readily ascertain the essential characteristics of this invention, and without departing from the spirit and scope thereof, can make various changes and/or modifications of the invention to adapt it to various usages and conditions.

What is claimed:

1. A system for providing laser shot patterns to an eye, for the correction of induced astigmatic aberrations of the eye, the system comprising:
   a therapeutic laser for producing a laser beam;
   a controller configured to deliver a first laser shot pattern, a second laser shot pattern, and a third laser shot pattern;
   optics for receiving the laser beam and directing the laser beam to an eye to generate the first and the second shot patterns, wherein 1) the first laser shot pattern comprises a pattern for preforming an ophthalmic surgical procedure; 2) the second laser shot pattern comprises a pattern for sectioning a lens of an eye wherein one or more of the laser shot pattern for performing the ophthalmic surgical procedure and the laser shot pattern for sectioning a lens of an eye causes induced astigmatism to the eye; and 3) the third laser shot pattern for providing a sub-Bowman's membrane arcuate cut in a cornea of the eye, whereby the third laser pattern does not disrupt Bowman's membrane of the eye or an epithelium of the eye and reduces the induced astigmatism of the eye.

2. The system of claim 1, wherein the sub-Bowman's membrane arcuate pattern is oriented along a steep axis so as to be intersected by the steep axis.

3. The system of claim 1, wherein the sub-Bowman's membrane arcuate pattern has about a 3 mm radius.

4. The system of claim 1, wherein the sub-Bowman's membrane arcuate pattern has an arc of about 60°.

5. The system of claim 1, wherein the sub-Bowman's membrane arcuate pattern has an arc of about 90°.

6. The system of claim 1, wherein the sub-Bowman's membrane arcuate pattern has an arc of about less than 90° and about greater than or equal to 60°.

7. The system of claim 1, wherein the sub-Bowman's membrane arcuate pattern has about a 3 mm radius and an arc of about 90° to about 60°.

8. The system of claim 1, wherein the laser system provides the sub-Bowman's membrane arcuate cut in a manner that does not disrupt the Bowman's membrane of the eye.

9. The system of claim 1, wherein the laser system provides the sub-Bowman's membrane arcuate cut in a manner that does not disrupt the epithelium of the eye.

10. The system of claim 1, wherein the laser system provides the sub-Bowman's membrane arcuate cut in a manner that does not disrupt both the Bowman's membrane of the eye and the epithelium of the eye.

* * * * *